March 12, 1963 C. FISCHER Plant Pat. 2,234
GLADIOLUS PLANT
Filed April 12, 1962
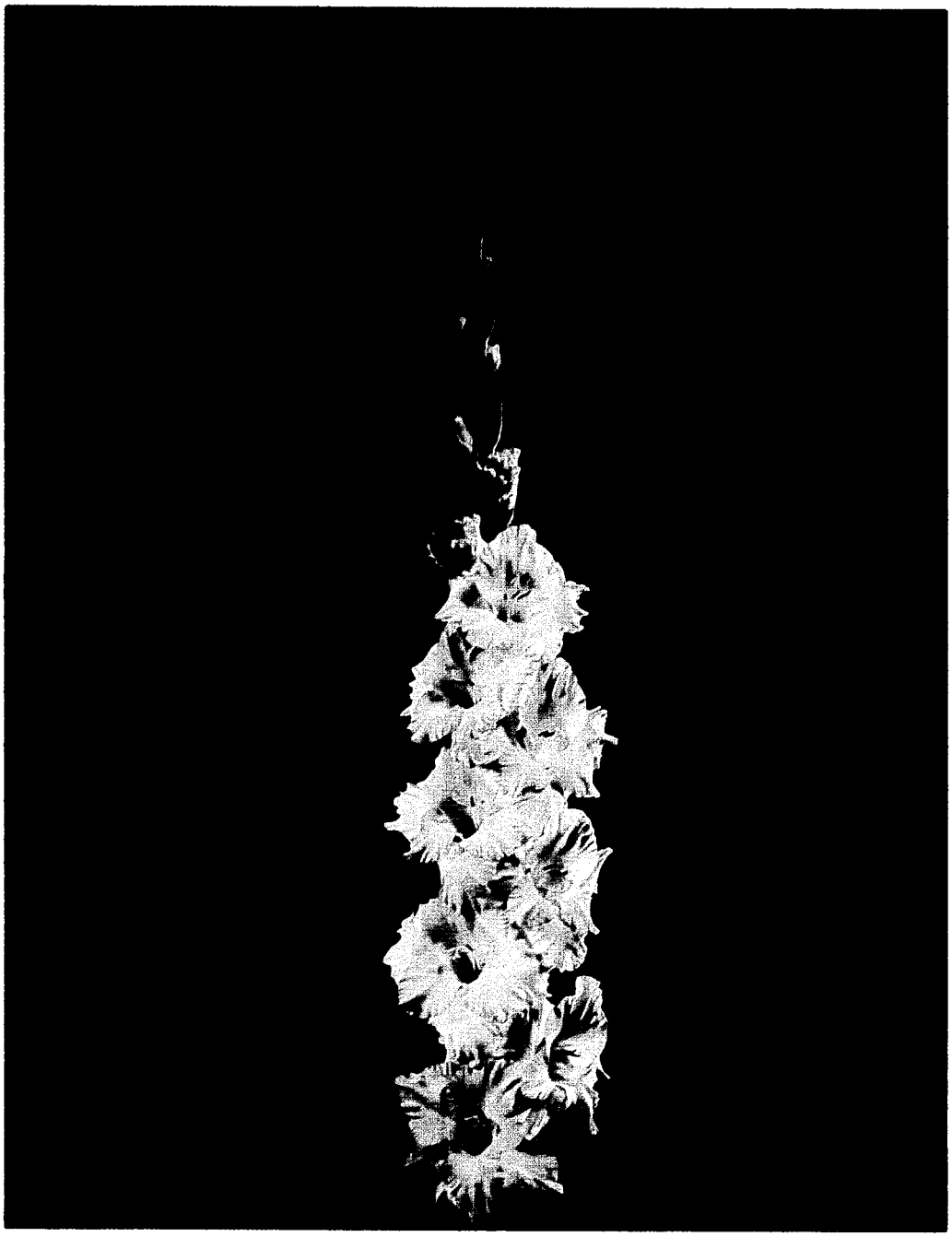
Inventor.
Carl Fischer
By: Robb & Robb
Attorneys.

United States Patent Office

Plant Pat. 2,234
Patented Mar. 12, 1963

2,234
GLADIOLUS PLANT

Carl Fischer, St. Charles, Minn., assignor to Imperial Flowers Limited, Leamington, Ontario, Canada, a corporation of Canada Filed Apr. 12, 1962, Ser. No. 187,140
1 Claim. (Cl. 47—60)

The present invention relates to a new and distinct variety of gladiolus plant which was originated by me by crossing the variety "Prospector" (unpatented) with the variety "Golden Sunshine" (unpatented), "Prospector" being the seed parent and "Golden Sunshine" the pollen parent.

The primary objective of this breeding was to produce a new gladiolus variety, characterized by outstanding beauty. This objective was fully achieved, along with other desirable features, as evidenced by the following unique combination of characteristics which are outstanding in the new variety and which distinguish it from its parents, as well as from all other varieties of which I am aware:

(1) Heavy flower petal substance;

(2) An attractive flower form which appears to be sharply carved or chiseled;

(3) Extremely ruffled flower petals; and (4) A distinctive and attractive yellow general color tonality of the flowers which greatly contributes to the overall supreme beauty thereof.

My new variety resembles "Lorelei" (unpatented) more than any other known variety, but differs therefrom principally by a flower opening habit which is better from the tight bud; more recurved flower petals; broader and rounder flower petals; more ruffling of the flower petals; heavier substance of the flower petals; and a more beautiful and appealing appearance of the flowers as a whole.

Asexual reproduction of the new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Rugged; blossom spike attains height averaging from 60 inches to 64 inches; excellent propagator.

Blooming habit: Rather late bloomer in the northern latitudes of the United States; comes into bloom from the planting of large bulbs in about 90 days.

Stems: Straight and stiff.

*Diameter at base.*—⅜ inch.

*Color (just above the bulb).*—Rosy purple.

Foliage: Upright; fan-shaped; attains height of from 40 inches to 46 inches; leaves range from 1½ inches to 2½ inches wide. Color—healthy green.

Disease resistance: Unusually resistant to Fusarium yellows, Sclerotina dry rot and Septoria leaf spot, as determined by comparison with other varieties grown in my fields near St. Charles, Minnesota, in irrigated black loam soil.

Corms (bulbs): Normal; round; plump. Color of flesh—Apricot, Plate 609/1.

*Flower*

Spike: Tall; stiff; straight; bears from 20 to 22 buds, with from 7 to 9 buds opening at once and with from 5 to 7 showing color at one time; flower head ranges from 24 inches to 26 inches long, and has a carved, statue-like appearance.

Bud:

*Size.*—From 2½ inches to 3 inches long when opening.

*Opening.*—From 5 to 7 buds show color at one time.

Flower:

*Arrangement.*—Flowers are formally arranged on the stem in a double row and usually all face forward.

*Size.*—Individual florets range from 4¾ inches to 5 inches in diameter; upper blooms progressively smaller.

*Form.*—Florets are round, recurved and heavily ruffled.

*Keeping qualities.*—An especially good opener from tight bud.

Petals:

*Shape.*—Round; intensely and precisely ruffled; gracefully recurved.

*Size.*—Outer petals—from 2 inches to 2¼ inches wide. Lip petal—1¼ inches wide.

*Aspect.*—Extremely heavy and leathery substance.

*Fragrance.*—None.

*Color.*—Naples Yellow, Plate 403/3 in general effect, with some petals creamy white and slightly deeper on lip petals; slightly open florets more nearly Empire Yellow, Plate 603/3; lip blotches are Uranium Green, Plate 63/3; florets usually fade from second day.

*Reproductive Organs*

Stamens: Color—lavender-purple.

Pistil: Color—creamy white.

I claim:

A new and distinct variety of gladiolus plant, substantially as herein shown and described, characterized particularly as to novelty by the unique combination of a heavy flower petal substance, a flower form which presents a carved or chiseled appearance, an extremely intense and precise ruffling of the flower petals, and a distinctive and attractive yellow general color tonality of the flowers which materially contributes to the over-all supreme beauty thereof.

No references cited.